(12) United States Patent
Selvaraj et al.

(10) Patent No.: US 11,833,119 B2
(45) Date of Patent: Dec. 5, 2023

(54) COMBINATION THERAPIES FOR THE TREATMENT OF HEPATOCELLULAR CARCINOMA

(71) Applicant: Eisai R&D Management Co., Ltd., Tokyo (JP)

(72) Inventors: Anand Selvaraj, Cambridge, MA (US); Peter Smith, Arlington, MA (US)

(73) Assignee: EISAI R&D MANAGEMENT CO., LTD., Tokyo (JP)

(*) Notice: Subject to any disclaimer, the term of this patent is extended or adjusted under 35 U.S.C. 154(b) by 0 days.

(21) Appl. No.: 16/961,292

(22) PCT Filed: Jan. 9, 2019

(86) PCT No.: PCT/US2019/012886
§ 371 (c)(1),
(2) Date: Jul. 10, 2020

(87) PCT Pub. No.: WO2019/139977
PCT Pub. Date: Jul. 18, 2019

(65) Prior Publication Data
US 2020/0360371 A1    Nov. 19, 2020

Related U.S. Application Data

(60) Provisional application No. 62/615,848, filed on Jan. 10, 2018.

(51) Int. Cl.
*A61K 31/496* (2006.01)
*A61P 35/00* (2006.01)
*A61K 31/4375* (2006.01)

(52) U.S. Cl.
CPC ........ *A61K 31/496* (2013.01); *A61K 31/4375* (2013.01); *A61P 35/00* (2018.01)

(58) Field of Classification Search
None
See application file for complete search history.

(56) References Cited

U.S. PATENT DOCUMENTS

| 7,253,286 | B2 | 8/2007 | Funahashi et al. |
| 7,612,208 | B2 | 11/2009 | Matsushima et al. |
| 9,006,256 | B2 | 4/2015 | Matsui |
| 9,434,697 | B2 * | 9/2016 | Reynolds ............. C07D 403/12 |
| 10,736,900 | B2 * | 8/2020 | Jovcheva ............. A61K 31/519 |
| 2010/0239688 | A1 | 9/2010 | Yamamoto |
| 2014/0378422 | A1 | 12/2014 | Yovine et al. |
| 2015/0005343 | A1 | 1/2015 | Nomoto et al. |
| 2016/0089365 | A1 | 3/2016 | Kato et al. |

FOREIGN PATENT DOCUMENTS

| CN | 101848895 A | 9/2010 |
| CN | 104093402 A | 10/2014 |
| CN | 105338977 A | 2/2016 |
| CN | 106456648 A | 2/2017 |
| CN | 107304188 A | 10/2017 |
| WO | 2015057938 A1 | 4/2015 |
| WO | 2016168331 A1 | 10/2016 |
| WO | 2017196854 A1 | 11/2017 |

OTHER PUBLICATIONS

Eisai Clinical Study Protocol (2016). (Year: 2016).*
Kudo et al. (Liver Cancer, 2017, 6, 253-263). (Year: 2017).*
Berge, et al., "Pharmaceutical Salts", J. Pharm. Sci., Jan. 1977, vol. 66, No. 1, pp. 1-19.
Chou, et al., "Quantitative analysis of dose-effect relationships: the combined effects of multiple drugs or enzyme inhibitors", Adv. Enzyme Regul., 1984 (month unknown), vol. 22, pp. 27-55.
Holford, et al., "Understanding the dose effect relationship: Clinical application of pharmacokinetic-phatmacodynamic", Clin. Pharmacokinet., 1981 (month unknown), vol. 6, pp. 429-453.
International Search Report (PCT/ISA/210) and Written Opinion (PCT/ISA/237) dated Apr. 23, 2019, by the European Patent Office as the International Searching Authority for International Application No. PCT/US2019/012886.
Joshi, et al., "H3B-6527 Is a Potent and Selective Inhibitor of FGFR4 in FGF19-Dri ven Hepatocellular Carcinoma", Cancer Research, Dec. 2017, vol. 77, No. 24, pp. 6999-7013.
Kudo, "A New Era of Systemic Therapy for Hepatocellular Carcinoma with Regorafenib and Lenvatinib", Liver Cancer, Jan. 2017, vol. 6, No. 3, pp. 177-184.
"2b or Not 2b: How Opposing FGF Receptor Splice Variants Are Blocking Progress in Precision Oncology" Richard J. Epstein, Li Jun Tian, Yan Fei Gu; Journal of Oncologyvol. 2021, Article ID 9955456, 16 pages, https://doi.org/10.1155/2021/9955456.
"FGF/FGFR signaling in health and disease" Yangli Xie, et al., Signal Transduction and Targeted Therapy (2020) 5:181; https://doi.org/10.1038/s41392-020-00222-7.
"A Network Map of FGF-1/FGFR Signaling System" Rajesh Raju, et al.; Hindawi Publishing Corporation, Journal of Signal Transduction, vol. 2014, Article ID 962962, 16 pages, http://dx.doi.org/10.1155/2014/962962.
"The Fibroblast Growth Factor signaling pathway" David M. Omitz and Nobuyuki Itoh; WIREs Dev Biol 2015, 4:215-266. doi: 10.1002/wdev.176, vol. 4, May/Jun. 2015, 2015 Wiley Periodicals, Inc.
"Evaluation of BGJ398, a Fibroblast Growth Factor Receptor 1-3 Kinase Inhibitor, in Patients With Advanced Solid Tumors Harboring Genetic Alterations in Fibroblast Growth Factor Receptors: Results of a Global Phase I, Dose-Escalation and Dose-Expansion Study" Lucia Nogova, et al.; Journal of Clinical Oncology; vol. 35, No. 2, Jan. 10, 2017; Downloaded from ascopubs.org by EISAI Medical Research Inc on May 14, 2018 from 209.255.224.071 Copyright © 2018 American Society of Clinical Oncology.
"Discovery of 3-(2,6-Dichloro-3,5-Dimethoxy-phenyl)-1-(6-14-(4-ethyl-piperazin-1-yl)-phenylaminol-pyrimidin-4-yl}-1-methyl-urea (NVP-BGJ398), a Potent and Selective Inhibitor of the Fibroblast Growth Factor Receptor Family of Receptor Tyrosine Kinase" Vito Guagnano, et al.; Novartis Institute for BioMedical Research, Journal of Medical Chemistry, J. Med. Chem. 2011, 54, 7066-7083.

(Continued)

*Primary Examiner* — Celeste A Roney
(74) *Attorney, Agent, or Firm* — BUCHANAN INGERSOLL & ROONEY PC (57) ABSTRACT

Provided herein is a combination therapy useful for the treatment hepatocellular carcinoma. The combination comprises an FGFR4 inhibitor and lenvatinib.

18 Claims, 2 Drawing Sheets

(56) References Cited

OTHER PUBLICATIONS

"Fibroblast Growth Factor Receptors (FGFRs): Structures and Small Molecule Inhibitors" Shuyan Dai, et al.; Cells 2019, 8, 614; doi:10.3390/cells8060614; www.mdpi.com/journal/cells.

"In-silico Prediction of Synergistic Anti-Cancer Drug Combinations Using Multi-omics Data" Remzi Celebi et al.; Scientific Reports; www.nature.com/scientificreports; (2019) 9:8949 | https://doi.org/10.1038/s41598-019-45236-6.

"Cancers of the Pancreas, Small Bowel, and Hepatobiliary Tract: Phase III randomized study of sorafenib plus doxorubicin versus sorafenib in patients with advanced hepatocellular carcinoma (HCC): CALGB 80802 (Alliance)" Journal of Clinical Oncology, vol. 34, Issue 4 suppl., https://ascopubs.org/doi/abs/10.1200/jco.2016.34.4_suppl.192.

"Lenvatinib, an angiogenesis inhibitor targeting VEGFR/FGFR, shows broad antitumor activity in human tumor xenograft models associated with microvessel density and pericyte coverage" Yamamoto et al., Vascular Cell 2014, 6:18 http://www.vascularcell.com/content/6/1/18.

"Identification of Pharmacodynamic Transcript Biomarkers in Response to FGFR Inhibition by AZD4547" Oona Delpuech, et al.; Molecular Cancer Therapeutics; 2802 Mol Cancer Ther; 15(11) Nov. 2016; downloaded mct.aacrjournals.org on Oct. 16, 2021.

"Aberrant FGFR signaling mediates resistance to CDK4/6 inhibitors in ER+ breast cancer" Luigi Formisano, et al., Nature Communications, (2019) 10:1373 | https://doi.org/10.1038/s41467-019-09068-2, www.nature.com/naturecommunications.

"Comprehensive transcriptomic analysis of molecularly targeted drugs in cancer for target pathway evaluation" Tetsuo Mashima, et al.; Cancer Science, Jul. 2015, vol. 106, No. 7, 909-920.

"E7080, a novel inhibitor that targets multiple kinases, has potent antitumor activities against stem cell factor producing human small cell lung cancer H146, based on angiogenesis inhibition" Junji Matsui, et al.; Int. J. Cancer: 122, 664-671 (2008); Publication of the International Union Against Cancer.

"Multi-Kinase Inhibitor E7080 Suppresses Lymph Node and Lung Metastases of Human Mammary Breast Tumor MDA-MB-231 via Inhibition of Vascular Endothelial Growth Factor-Receptor (VEGF-R) 2 and VEGF-R3 Kinase" Junji Matsui, et al.; Cancer Therapy: Preclinical; Clin Cancer Res 2008; 14(17) Sep. 1, 2008; www.aacrjournals.org.

"FGF19-FGFR4 Signaling in Hepatocellular Carcinoma" Aroosha Raja, et al.; Cells 2019, 8, 536; doi:10.3390/cells8060536; www.mdpi.com/journal/cells.

Harkevich D.A., "Pharmacology", textbook, 10th edition. M: Geotar Media, 2010, pp. 73-74.

Zhulenko V.N. et al., "Pharmacology", textbook, Moscow: KolosS, 2008, pp. 34-35.

Ikeda M. et al., "Safety and Pharmacokinetics of Lenvatinib in Patients with Advanced Hepatocellular Carcinoma", Clinical Cancer Research, 2016, 22(6), pp. 1385-1394.

Ikeda K. et al., "Phase 2 study of lenvatinib in patients with advanced hepatocellular carcinoma", J Gastroenterol., 2017, 52(4), pp. 512-519.

Office Action dated Apr. 19, 2022, issued in the corresponding Russian Patent Application No. 2020126673, with English Translation, 12 pages.

Office Action dated Apr. 7, 2023, by China National Intellectual Property Administration in corresponding Chinese Patent Application No. 201980015321X and an English translation fo the Office Action (12 pages).

Office Action dated Oct. 31, 2022, by the State Intellectual Property Office of People's Republic of China in corresponding Chinese Patent Application No. 201980015321.X and an English translation of the Office Action. (13 pages).

Office Action (Notice of Deficiencies) dated Dec. 21, 2022, by the Israel Patent Office in corresponding Israeli Patent Application No. 275981. (4 pages).

Office Action (Notice of Reasons for Refusal) dated Jan. 17, 2023, by the Japan Patent Office in corresponding Japanese Patent Application No. 2020-558858 and an English translation of the Office Action. (4 pages).

\* cited by examiner

COMBINATION THERAPIES FOR THE TREATMENT OF HEPATOCELLULAR CARCINOMA

CROSS-REFERENCE TO RELATED APPLICATIONS

This application claims benefit of U.S. Provisional Patent Application No. 62/615,848, filed on Jan. 10, 2018. That application is incorporated by reference as if fully rewritten herein.

BACKGROUND

Liver cancer is the second greatest cause of mortality from any type of cancer, and the 16th most common cause of death worldwide (Llovet J M, et al., 2015 "Advances in targeted therapies for hepatocellular carcinoma in the genomic era." *Nat. Rev. Clin Oncology* 12, 408-424). Hepatocellular carcinoma (HCC) accounts for up to 90% of all primary liver cancers (Llovet J M et al. 2015).

Compound 1 is a selective, orally bioavailable small molecule FGFR4 inhibitor with the structure shown in Formula I, and the chemical name N-(2-((6-(3-(2,6-dichloro-3,5-dimethoxyphenyl)-1-methylureido)pyrimidin-4-yl)amino)-5-(4-ethylpiperazin-1-yl)phenyl)acrylamide:

(I)

Compound 1 and its synthesis are reported in PCT International Application Publication No. WO2015/057938, published on Apr. 23, 2015. That document is incorporated by reference herein.

Lenvatinib (4-[3-chloro-4-(N'-cyclopropylureido)phenoxy]-7-methoxyquinoline-6-carboxamide) is a receptor tyrosine kinase (RTK) inhibitor that inhibits the kinase activities of vascular endothelial growth factor (VEGF) receptors VEGFR1 (FLT1), VEGFR2 (KDR), and VEGFR3 (FLT4). Lenvatinib also inhibits other RTKs that have been implicated in pathogenic angiogenesis, tumor growth, and cancer progression in addition to their normal cellular functions, including fibroblast growth factor (FGF) receptors FGFR1, 2, 3, and 4; the platelet derived growth factor receptor alpha (PDGFRα), KIT, and RET. Lenvatinib is reported in U.S. Pat. Nos. 7,253,286; 7,612,208; and 9,006,256; all of which are incorporated by reference herein.

Despite advances in the treatment of HCC, it would be useful to provide alternative treatment of HCC, including treatment for patients whose HCC may be resistant to, poorly responsive to, or not completely responsive to current therapeutic regimens.

SUMMARY

Embodiments provide a combination therapy, comprising an amount of Compound 1 and an amount of a lenvatinib in an effective amount in a patient in need of treatment for hepatocellular carcinoma (HCC). Combination therapy provided herein may lead to a synergistic reduction in the viability of HCC cells and may lead to tumor growth inhibition of HCC in patients in need of treatment.

DETAILED DESCRIPTION OF EMBODIMENTS

Provided herein are combination therapies useful in treating hepatocellular carcinoma (HCC). In some embodiments, the combination therapies include administration of Compound 1 in combination with lenvatinib.

Provided herein are combinations of therapeutic agents and methods for administration of the combination of agents to treat hepatocellular carcinoma. As used herein, a "combination of therapeutic agents" and similar terms refer to a combination of two types of therapeutic agents: (1) Compound 1 and/or pharmacologically active metabolites, salts, solvates, and racemates of Compound 1 and (2) lenvatinib and/or pharmacologically active metabolites, salts, solvates, and racemates of lenvatinib. Pharmacologically active metabolites comprise those that are inactive but converted into pharmacologically active forms in the body after administration.

Compound 1 is a selective, orally bioavailable small molecule FGFR4 inhibitor with the structure shown in Formula I:

(I)

Compound 1 and its synthesis are reported in PCT International Application Publication No. WO2015/057938, published on Apr. 23, 2015. That document is incorporated by reference herein.

Lenvatinib (4-[3-chloro-4-(N'-cyclopropylureido)phenoxy]-7-methoxyquinoline-6-carboxamide) is a receptor tyrosine kinase (RTK) inhibitor that inhibits the kinase activities of vascular endothelial growth factor (VEGF) receptors VEGFR1 (FLT1), VEGFR2 (KDR), and VEGFR3 (FLT4). Lenvatinib also inhibits other RTKs that have been implicated in pathogenic angiogenesis, tumor growth, and cancer progression in addition to their normal cellular functions, including fibroblast growth factor (FGF) receptors FGFR1, 2, 3, and 4; the platelet derived growth factor receptor alpha (PDGFRα), KIT, and RET. Lenvatinib has the following structure:

The mesylate salt of lenvatinib, known as LENVIMA® from Eisai, Inc., 4-[3-chloro-4-(N'-cyclopropylureido)phenoxy]-7-methoxyquinoline-6-carboxamide methanesulfonate, has the following structure:

Lenvatinib is reported in U.S. Pat. Nos. 7,253,286; 7,612,208; and 9,006,256; all of which are incorporated by reference herein.

Administration of a combination of therapeutic agents comprises administration of the individual therapeutic agents in combination in a single formulation or unit dosage form, administration of the individual therapeutic agents of the combination concurrently but separately, or administration of the individual agents of the combination sequentially by any suitable route. The dosage of the individual therapeutic agents of the combination may require more frequent administration of one of the agents as compared to the other agent in the combination. Therefore, to permit appropriate dosing, packaged pharmaceutical products may contain one or more dosage forms that contain the combination of agents, and one or more dosage forms that contain one of the combinations of agents, but not the other agent(s) of the combination.

Therapeutic agents may contain one or more asymmetric elements such as stereogenic centers or stereogenic axes, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms; all isomeric forms of the compounds are included in the present invention. In these situations, the single enantiomers (optically active forms) can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Combinations as reported herein may include embodiments wherein one or more of Compound 1 and lenvatinib are administered as a pharmaceutically acceptable salt or as a free base. There is no requirement that both compounds be administered as the same pharmaceutically acceptable salt, but they may be. In particular embodiments Compound 1 is administered as a hydrochloride salt and lenvatinib is administered as a mesylate salt.

"Pharmaceutically acceptable salt" as used herein refers to acid addition salts or base addition salts of the compounds in the present disclosure. A pharmaceutically acceptable salt is any salt which retains the activity of the parent compound and does not impart any unduly deleterious or undesirable effect on a subject to whom it is administered and in the context in which it is administered. Pharmaceutically acceptable salts include, but are not limited to, metal complexes and salts of both inorganic and carboxylic acids. Pharmaceutically acceptable salts also include metal salts such as aluminum, calcium, iron, magnesium, manganese and complex salts. In addition, pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycolic, glycolylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methyl sulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like.

Embodiments may include hydrochloride salts of Compound 1. Pharmaceutically acceptable salts may be derived from amino acids including, but not limited to, cysteine. Methods for producing compounds as salts are known to those of skill in the art (see, e.g., Stahl et al., Handbook of Pharmaceutical Salts: Properties, Selection, and Use, Wiley-VCH; Verlag Helvetica Chimica Acta, Zurich, 2002; Berge et al., J. Pharm. Sci. 66: 1, 1977).

An "effective amount" of a combination of therapeutic agents (e.g., Compound 1 and lenvatinib) is an amount sufficient to provide an observable therapeutic benefit compared to baseline HCC.

Active agents as reported herein can be combined with a pharmaceutically acceptable carrier to provide pharmaceutical formulations thereof. The particular choice of carrier and formulation will depend upon the particular route of administration for which the composition is intended.

"Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, sorbic acid, potassium sorbate, partial glyceride mixtures of saturated vegetable fatty acids, water, salts or electrolytes, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene glycol and wool fat.

The compositions of the present invention may be suitable for parenteral, oral, inhalation spray, topical, rectal, nasal, buccal, vaginal or implanted reservoir administration, etc. In some embodiments, the formulation comprise ingredients that are from natural or non-natural sources. In some embodiments, the formulation or carrier may be provided in a sterile form. Non-limiting examples of a sterile carrier include endotoxin-free water or pyrogen-free water.

The term "parenteral" as used herein includes subcutaneous, intravenous, intramuscular, intra-articular, intra-synovial, intrasternal, intrathecal, intrahepatic, intralesional and intracranial injection or infusion techniques. In particular embodiments, the compounds are administered intravenously, orally, subcutaneously, or via intramuscular administration. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids and their glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents that are commonly used in the manufacture of pharmaceutically acceptable solid, liquid, or other dosage forms may also be used for the purposes of formulation.

For oral administration, a compound or salt may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient may be combined with emulsifying and suspending agents. If desired, certain sweetening, flavoring or coloring agents may also be added. In addition preservatives may also be added. Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

"Immediate-release" is meant to include a conventional release, in which release of the drug starts immediately after administration. As used herein, the term "immediate release" includes dosage forms that allow the drug to dissolve in the gastrointestinal contents, with no intention of delaying or prolonging the dissolution or absorption of the drug. The objective is for the drug to be released rapidly after administration, for example for it to be possible to release at least 80% of the drug within approximately 30 minutes after commencement of dissolution in a dissolution test.

"Sustained-release" or "extended-release" includes dosage forms whose drug-release characteristics of time course and/or location are chosen to accomplish therapeutic or convenience objectives not offered by conventional dosage forms such as a solution or an immediate release dosage form.

The term "steady-state" means that a plasma level for a given active agent or combination of active agents, has been achieved and which is maintained with subsequent doses of the active agent(s) at a level which is at or above the minimum effective therapeutic level and is below the minimum toxic plasma level for a given active agent(s).

The term "single formulation" as used herein refers to a single carrier or vehicle formulated to deliver effective amounts of both therapeutic agents to a patient. The single vehicle is designed to deliver an effective amount of each of the agents along with any pharmaceutically acceptable carriers or excipients. In some embodiments, the vehicle is a tablet, capsule, pill, or a patch.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents (levantinib or Compound 1) along with pharmaceutically acceptable carriers and excipients. In some embodiments, the unit dose is one or more tablets, capsules, pills, or patches administered to the patient at the same time.

The term "dose range" as used herein refers to an upper and a lower limit of an acceptable variation of the amount of agent specified. Typically, a dose of an agent in any amount within the specified range can be administered to patients undergoing treatment.

The term "treat" is used herein to mean to relieve, reduce or alleviate at least one symptom of a disease in a subject. For example, in relation to HCC, the term "treat" may mean to arrest, delay the onset (i.e., the period prior to clinical manifestation of a disease or symptom of a disease) and/or reduce the risk of developing or worsening a symptom of a disease. The term "protect" is used herein to mean prevent delay or treat, or all, as appropriate, development or continuance or aggravation of symptoms of the disease in a subject.

The term "subject" is intended to include animals, which are capable of suffering from or afflicted with HCC. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from HCC.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

The term "synergistic effect" as used herein, refers to action of two agents such as, for example, Compound 1 and lenvatinib, producing an effect, for example, slowing the progression of HCC, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

In some embodiments, treatment is provided to a subject having hepatocellular carcinoma with altered FGFR4 and/or FGF19 (fibroblast growth factor 19) status.

In some embodiments, treatment may include or be performed in conjunction with analyzing FGFR4 and/or FGF19 status in a biological sample containing cells of said hepatocellular carcinoma, and if said hepatocellular carcinoma exhibits an FGFR4 and/or FGF19 alteration, treating a subject with a treatment effective amount of a therapeutic combination as described herein.

In order that embodiments described herein may be more fully understood, the following examples are set forth. It should be understood that these examples are for illustrative purposes only and are not to be construed as limiting.

Methods of Treatment

Provided herein is a combination therapy useful for the treatment of HCC. As discussed below, combinations provided herein may have a number of advantages.

One advantage of the combination disclosed herein is the unexpected synergistic effect of a combination of Compound 1 and lenvatinib on treatment of tumor growth inhibition and treatment of HCC.

In some embodiments, provided herein is a single pharmaceutical formulation containing a combination of Compound 1 and lenvatinib. An advantage provided herein is the synergistic effect that results in the treatment of HCC compared to treatment with a single dose of either drug. When the drugs are provided in a single unit dose or single formulation, the "pill burden" on a patient suffering from HCC is not increased.

As specified above, in one aspect, provided herein is a drug combination useful for treating, preventing, arresting, delaying the onset of and/or reducing the risk of developing, or reversing HCC in a mammal comprising administering to said mammal a combination therapy, comprising Compound 1 and lenvatinib, together in an effective amount.

In some embodiments, the subject to be treated (e.g., patient) is determined to be non-responsive or resistant to one or more HCC therapies, e.g., Compound 1. In other embodiments, the individual to be treated is responsive to Compound 1 therapy, but the therapy is improved with the administration of lenvantinib. For example, the patient is administered Compound 1 (e.g., 50 mg to 600 mg per day, 200 mg to 400 mg per day, or 300 mg per day) for some period of time, e.g., more than one day, more than two days, more than three days, more than one week, more than one month, etc. After that time, lenvatinib could be administered to that patient in combination with Compound 1.

Amounts of lenvatinib may vary. For example, lenvatinib may be administered in an amount of 8 mg/day or 12 mg/day The daily dosage may be part of a cyclic regimen lasting 14 to 21 days or longer. The daily dosage amount may be administered as a single dosage or as multiple dosages.

One skilled in the art appreciates that the effective dose of the active drug may be lower than the actual amount administered. As such, provided herein are doses necessary to achieve a therapeutic dose.

In various embodiments, provided herein are methods of treating HCC by administering an effective amount of Compound 1 and lenvatinib, to an individual having HCC. The amount of the combination of agents is effective to treat the HCC. In one embodiment, the combination of agents has a synergistic effect. In one embodiment, even though one or more of the agents administered alone at a particular dosage may be effective, when administered in combination, at the same dosage of each agent, the treatment is more effective. For example, in one embodiment a combination of Compound 1 and lenvatinib is more effective than is administration of either agent alone.

Dosages

The optimal dose of the combination of agents for treatment of HCC can be determined empirically for each individual using known methods and will depend upon a variety of factors, including the activity of the agents; the age, body weight, general health, gender and diet of the individual; the time and route of administration; and other medications the individual is taking. Optimal dosages may be established using routine testing and procedures that are well known in the art.

For the combination therapy of the instant invention, the daily dose of Compound 1 is in the range of 50 mg to 600 mg. In some embodiments, the daily dose of Compound 1 is up to 600 mg. In certain embodiments, the daily dose of Compound 1 is up to 400 mg. In various embodiments, the daily dose of Compound 1 is up to 300 mg. In certain embodiments, the daily dose of Compound 1 is 200 mg to 400 mg. In one embodiment, the daily dose is 300 mg.

In certain embodiments, the daily dose of lenvatinib is 8 mg. In certain embodiments, the daily dose of lenvatinib is 12 mg. In certain embodiments, the daily dose of lenvatinib is between 7 mg and 13 mg. In certain embodiments, the daily dose of lentabinib is between 8 mg and 12 mg.

The time of administration can be chosen such that both the drugs are administered simultaneously, separately or sequentially, either in the morning or at night. Alternatively, one drug can be administered in the morning and the other at night. In certain embodiments, both the drugs can be administered as a single tablet, capsule, pill, patch or jelly formulation, once daily, either in the morning or at night.

The amount of combination of agents that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Pharmaceutical Formulations and Routes of Administration

Provided herein are pharmaceutical formulations comprising a combination of agents for the treatment of HCC.

The pharmaceutical formulations may additionally comprise a carrier or excipient, stabilizer, flavoring agent, and/or coloring agent.

A combination of agents may be administered using a variety of routes of administration known to those skilled in the art. Routes of administration include oral administration. In certain embodiments, a pharmaceutical formulation comprising a combination of agents may be taken orally in the form of liquid, syrup, tablet, capsule, powder, sprinkle, chewtab, or dissolvable disk. Alternatively, pharmaceutical formulations of the present invention can be administered intravenously or transdermally. Additional routes of administration are known to those skilled in the art (see, e.g., Remington's Pharmaceutical Sciences, Gennaro A. R., Ed., 20.sup.th Edition, Mack Publishing Co., Easton, Pa.).

In some embodiments, the Compound 1 and lenvatinib are formulated as a paste, jelly, or suspension. For example, the drugs are dissolved, entrapped or suspended in the form of drug particles, microencapsulated particles, or drug-polymer particles in a gelatinous solution or semi-solid. An advantage of an oral jelly formulation is that it is easier to administer the drugs to patients who have difficulty swallowing tablets, capsules or pills. In certain embodiments, both agents are thoroughly mixed and suspended in an appropriate medium to form a paste or a gel. Additional agents can optionally be mixed to provide flavor during oral administration. Peanut butter or alginate, flavored with raspberry and a sweetener are examples of the many suitable taste masking agents. In various embodiments, the paste or jelly can also be formulated with suitable binders or excipients known in the art for topical administration.

Methods of preparing sustained release formulations in the form of tablets, capsules or pills are known in the art. In some embodiments, the sustained release formulation is prepared by coating the active ingredient of the drug with a polymer, preferably a water-insoluble polymer. For example, a water-insoluble polymer used in the pharmaceutical field as a sustained release coating agent, an enteric coating agent, or a gastric coating agent. The water-insoluble polymer can include, for example, ethyl cellulose, purified shellac, white shellac, aminoalkyl methacrylate copolymer RS, hydroxypropyl methylcellulose phthalate, hydroxypropyl methylcellulose acetate succinate, carboxymethylethylcellulose, cellulose acetate phthalate, methacrylic acid copolymer L, methacrylic acid copolymer LD, methacrylic acid copolymer S, aminoalkyl methacrylate copolymer E, or polyvinyl acetal diethylaminoacetate.

The type, degree of substitution and molecular weight of the water-insoluble polymers can depend on solubility of the active ingredient in water or an alcohol, the desired sustained release level and the like. The water-insoluble polymers can be used either alone or in combination. There can be further incorporated a hydrogenated oil, stearic acid, or cetanol as a coating auxiliary agent, and a middle-chain triglyceride, triacetin, triethyl citrate, or cetanol as a plasticizer.

In some embodiments, the sustained release formulation is a matrix-type tablet or granule. The active ingredient can be coated with up to 3 different types of polymers. These three different types of polymers can include: 1) a water insoluble polymer, such as ethylcellulose; 2) a pH independent gelling polymer, such as hydroxypropyl methylcellulose; and 3) a pH dependent gelling polymer, such as sodium alginate. These three different types of polymers can be used together to attenuate the release rate of the drugs.

Dosage Forms: Release Properties

Sustained-release formulations can achieve a degree of sustained effect. However, the exposure and/or the bioavailability of the active ingredient may vary based on a variety of factors, such as for example, the absorption window, the carriers or excipients used in the formulation, the mode of delivery of the formulation, and/or the transit time of the active ingredient through the gastrointestinal tract of the patient.

A combination therapy can contain at least one sustained-release portion for performing a sustained-release function and one immediate release portion for performing an immediate release function. In certain embodiments, when the combination therapy is in a single dosage form, it can be in the form of tablets formed from a mixture of sustained-release granules constituting a sustained-release portion and immediate-release granules constituting an immediate-release portion, a capsule preparation obtained by filling a capsule with sustained-release granules and immediate-release granules, or press-coated tablets in which an outer layer constituting an immediate-release portion is formed on an inner core constituting a sustained-release portion. There is, however, no limitation to the above embodiments.

Moreover, there are no particular limitations on the state of containment of each drug in the composition or in an immediate-release portion or a sustained-release portion; the Compound 1 may be dispersed uniformly in the composition, immediate release portion or sustained release portion, or may be contained in only one part of the composition, immediate-release portion or sustained-release portion, or may be contained such that there is a concentration gradient.

A sustained-release portion in the composition according to the present invention can contain at least one non-pH-dependent polymeric substance or pH-dependent polymeric substance for controlling drug release.

A non-pH-dependent polymeric substance used herein can comprise a polymeric substance whose charge state hardly changes under pH conditions generally found in the gastrointestinal tract, specifically from pH 1 to pH 8. This means, for example, a polymeric substance that does not have functional groups whose charge state changes depending on the pH such as basic functional groups such as amino groups or acidic functional groups such as carboxylic acid groups. Note that the non-pH-dependent polymeric substance can be included for giving the composition according to the present invention a sustained-release function, but may also be included for another purpose. Moreover, the non-pH-dependent polymeric substance used in the present invention may be water-insoluble, or may swell in water or dissolve in water to form a gel.

Examples of water-insoluble non-pH-dependent polymeric substances include, but are not limited to, cellulose ethers, cellulose esters, and methacrylic acid-acrylic acid copolymers (trade name Eudragit, manufactured by Rohm GmbH & Co. KG, Darmstadt, Germany). Examples include, but are not limited to, cellulose alkyl ethers such as ethylcellulose (trade name Ethocel, manufactured by Dow Chemical Company, USA), ethyl methylcellulose, ethyl propylcellulose or isopropylcellulose, and butylcellulose, cellulose aralkyl ethers such as benzyl cellulose, cellulose cyanoalkyl ethers such as cyanoethylcellulose, cellulose organic acid esters such as cellulose acetate butyrate, cellulose acetate, cellulose propionate or cellulose butyrate, and cellulose acetate propionate, ethyl acrylate-methyl methacrylate copolymers (trade name Eudragit NE, manufactured by Rohm GmbH & Co. KG, Darmstadt, Germany), and aminoalkyl methacrylate copolymer RS (trade names Eudragit RL, Eudragit RS). There are no particular limitations on the mean particle diameter of a water-insoluble polymer used in the present invention, but usually the lower this mean particle diameter the better the performance, with the mean particle diameter preferably being from 0.1 to 100 µm, more preferably from 1 to 50 µm, particularly preferably from 3 to 15 µm, most preferably from 5 to 15 µm. Moreover, examples of water-soluble or water-swelling non-pH-dependent polymeric substances include, but are not limited to, polyethylene oxide (trade name Polyox, manufactured by Dow Chemical Company, molecular weight 100,000 to 7,000,000), low-substituted hydroxypropyl cellulose (trade name L-HPC, manufactured by Shin-Etsu Chemical, Japan), hydroxypropyl cellulose (trade name HPC, manufactured by Nippon Soda, Co., Ltd, Japan), hydroxypropyl methylcellulose (trade names Metolose 60SH, 65SH, 90SH, manufactured by Shin-Etsu Chemical, Japan), and methylcellulose (trade name Metolose$^{SM}$, manufactured by Shin-Etsu Chemical, Japan).

In some embodiments a single non-pH-dependent polymeric substance may be contained in the composition, or a plurality of the non-pH-dependent polymeric substances may be contained. The non-pH-dependent polymeric substance, if used in embodiments reported herein, may be a water-insoluble polymeric substance, more preferably ethylcellulose, an ethyl acrylate-methyl methacrylate copolymer (trade name Eudragit NE), or an aminoalkyl methacrylate copolymer RS (trade name Eudragit RL, Eudragit RS). Particularly preferable is at least one of ethylcellulose and an aminoalkyl methacrylate copolymer RS. Most preferable is ethylcellulose. There are no particular limitations on the amount of the non-pH-dependent polymeric substance contained in the composition; this amount can be adjusted as appropriate in accordance with the purpose such as controlling sustained drug release.

A pH-dependent polymeric substance that can be used in embodiments reported herein may be a polymeric substance whose charge state changes under pH conditions generally found in the gastrointestinal tract, specifically from pH 1 to pH 8. This means, for example, a polymeric substance having functional groups whose charge state changes depending on the pH such as basic functional groups such as amino groups or acidic functional groups such as carboxylic acid groups. The pH-dependent functional groups of the pH-dependent polymeric substance are preferably acidic functional groups, with the pH-dependent polymeric substance most preferably having carboxylic acid groups.

A pH-dependent polymeric substance used in the present invention may be water-insoluble, or may swell in water or dissolve in water to form a gel. Examples of pH-dependent polymeric substances used in the present invention include, but are not limited to, enteric polymeric substances. Examples of enteric polymeric substances include, but are not limited to, methacrylic acid-methyl methacrylate copolymers (Eudragit L100, Eudragit S100, manufactured by Rohm GmbH & Co. KG, Darmstadt, Germany), methacrylic acid-ethyl acrylate copolymers (Eudragit L100-55, Eudragit L30D-55, manufactured by Rohm GmbH & Co. KG, Darmstadt, Germany), hydroxypropyl methylcellulose phthalate (HP-55, HP-50, manufactured by Shin-Etsu Chemical, Japan), hydroxypropyl methylcellulose acetate succinate (AQOAT, manufactured by Shin-Etsu Chemical, Japan), carboxymethyl ethylcellulose (CMEC, manufactured by Freund Corporation, Japan), and cellulose acetate phthalate.

Examples of pH-dependent polymeric substances that swell in water or dissolve in water to form a gel include, but are not limited to, alginic acid, pectin, carboxyvinyl polymer, and carboxymethyl cellulose. In the present invention, a single pH-dependent polymeric substance may be contained in the composition, or a plurality of pH-dependent polymeric substances may be contained. The pH-dependent polymeric substance used in the present invention is preferably an enteric polymeric substance, more preferably a methacrylic acid-ethyl acrylate copolymer, a methacrylic acid-methyl methacrylate copolymer, hydroxypropyl methylcellulose phthalate, or hydroxypropyl methylcellulose acetate succinate, particularly preferably a methacrylic acid-ethyl acrylate copolymer.

When using a pH-dependent polymeric substance in the manufacturing process of a composition according to the present invention, a commercially available product of a powder type or a granular type, or a suspension type in which the pH-dependent polymeric substance has been dispersed in a solvent in advance can be used as is, or such a commercially available product can be used dispersed in water or an organic solvent. The lower the particle diameter of the pH-dependent polymeric substance the better the performance, with the pH-dependent polymeric substance preferably being of the powder type. In the case of a methacrylic acid-ethyl acrylate copolymer, an example is Eudragit L100-55. There are no particular limitations on the mean particle diameter of a pH-dependent polymeric substance used in the present invention, but the mean particle diameter is preferably from 0.05 to 100 µm, more preferably from 0.05 to 70 µm, most preferably from 0.05 to 50 µm. Moreover, there are no particular limitations on the amount of the pH-dependent polymeric substance, for example, in the case of an enteric polymeric substance, the amount is generally from 0.1 to 90 parts by weight, preferably from 1 to 70 parts by weight, more preferably from 5 to 60 parts by weight, particularly preferably from 10 to 50 parts by weight, based on 100 parts by weight of the composition.

A combination therapy according to embodiments reported herein may further contain any of various additives, such as any of various pharmacologically acceptable carriers such as diluents, lubricants, binders and disintegrants, as well as preservatives, colorants, sweeteners, plasticizers, film coating agents and so on, as necessary. Examples of diluents include, but are not limited to, lactose, mannitol, dibasic calcium phosphate, starch, pregelatinized starch, crystalline cellulose, light silicic anhydride, synthetic aluminum silicate, magnesium aluminate metasilicate or the like. Examples of lubricants include, but are not limited to, magnesium stearate, calcium stearate, talc, sodium stearyl fumarate or the like. Examples of binders include, but are not limited to, hydroxypropyl cellulose, methylcellulose, sodium carboxymethyl cellulose, hydroxypropyl methylcellulose, polyvinylpyrrolidone or the like. Examples of disintegrants include, but are not limited to, carboxymethyl cellulose, calcium carboxymethyl cellulose, croscarmellose sodium, sodium carboxymethyl starch, low-substituted hydroxypropyl cellulose or the like. Examples of preservatives include, but are not limited to, paraoxybenzoic acid esters, chlorobutanol, benzyl alcohol, phenethyl alcohol, dehydroacetic acid, sorbic acid or the like. Preferable examples of colorants include, but are not limited to, water-insoluble lake pigments, natural pigments (e.g., .beta.-carotene, chlorophyll, red ferric oxide), yellow ferric oxide, red ferric oxide, black ferric oxide or the like. Preferable examples of sweeteners include, but are not limited to, sodium saccharin, dipotassium glycyrrhizate, aspartame, *stevia* or the like. Examples of plasticizers include, but are not limited to, glycerol fatty acid esters, triethyl citrate, propylene glycol, polyethylene glycol or the like. Examples of film coating agents include, but are not limited to, hydroxypropyl methylcellulose, hydroxypropyl cellulose or the like.

Manufacturing Methods

To manufacture embodiments as reported herein, a single conventional method, or a combination of conventional methods, can be used. For example, when manufacturing drug-containing granules as a sustained-release portion or an immediate-release portion, granulation is the main operation, but this may be combined with other operations such as mixing, drying, sieving, and classification. As the granulation method, for example, a wet granulation method in which a binder and a solvent are added to the powder and granulation is carried out, a dry granulation method in which the powder is compressed and granulation is carried out, a molten granulation method in which a binder that melts on heating is added and heating and granulation are carried out, or the like can be used.

Furthermore, in accordance with the granulation method, an operating method such as a mixing granulation method using a planetary mixer, a screw mixer or the like, a high-speed mixing granulation method using a Henschel mixer, a Super mixer or the like, an extruding granulation method using a cylindrical granulator, a rotary granulator, a screw extruding granulator, a pellet mill type granulator or the like, a wet high-shear granulation method, a fluidized-bed granulation method, a compression granulation method, a crushing granulation method, or a spraying granulation method can be used. After the granulation, drying using a dryer, a fluidized bed or the like, cracking, and sieving can be carried out to obtain the granules or fine granules for use. Moreover, a granulation solvent may be used when preparing the composition according to the present invention. There are no particular limitations on such a granulation solvent, which may be water or any of various organic solvents, for example, water, a lower alcohol such as methanol or ethanol, a ketone such as acetone or methyl ethyl ketone, methylene chloride, or a mixture thereof.

For sustained-release granules contained in embodiments, at least one drug and at least one selected from non-pH-dependent polymeric substances and pH-dependent polymeric substances are mixed together, a diluent and a binder are added as necessary, and granulation is carried out to obtain granular matter. The granular matter obtained is dried using a tray dryer, a fluidized bed dryer or the like, and sieving is carried out using a mill or an oscillator, whereby the sustained-release granules can be obtained. Alternatively, as a method of manufacturing sustained-release granules in the present invention, it is possible to add at least one drug, at least one selected from non-pH-dependent polymeric substances and pH-dependent polymeric substances, and as necessary a diluent and a binder using a dry compactor such as a roller compactor or a slug tabletting machine, and carry out compression-molding while mixing, and then carry out granulation by cracking down to a suitable size. The granular matter prepared using such a granulator may be used as is as granules or fine granules according to the present invention, or may be further cracked using a power mill, a roll granulator, a rotor speed mill or the like, and sieved to obtain sustained-release granules. Note that immediate-release granules can also be manufactured as for the sustained-release granules.

A compression-molded product can be manufactured as a drug-containing sustained-release portion or immediate-release portion, or as a composition reported herein using a single conventional method, or a combination of conventional methods. For example, at least one drug, at least one selected from non-pH-dependent polymeric substances and pH-dependent polymeric substances, a diluent such as mannitol or lactose, a binder such as polyvinylpyrrolidone or crystalline cellulose, a disintegrant such as carmellose sodium or crospovidone, and a lubricant such as magnesium stearate or talc are used, and tabletting is carried out using an ordinary method, whereby the compression-molded product can be obtained. In this case, tabletting is the main operation in the method of manufacturing the compression-molded product, but this may be combined with other operations such as mixing, drying, sugar coating formation, and coating.

Examples of the method for the tabletting include, but are not limited to, direct compression molding in which at least one drug and pharmacologically acceptable additives are mixed together and then the mixture is directly compression-molded into tablets using a tabletting machine, and dry granule compression or wet granule compression in which sustained-release granules or immediate-release granules according to the present invention are subjected to compression-molding after adding a lubricant or a disintegrant as necessary. There are no particular limitations on the tabletting machine used in the compression molding; for example, a single-punch tabletting machine, a rotary tabletting machine, or a press-coated tabletting machine can be used.

Drug-containing sustained-release granules or immediate-release granules, or compression-molded product according to embodiments herein can be used as is in the form of granules or a tablet as the composition, but may also be subjected to further processing to manufacture the composition. For example, the compression-molded product or granules can be given a film coating using a film base material such as ethylcellulose, casein, methylcellulose, hydroxypropyl methylcellulose, methacrylic acid copolymer L, cellulose acetate phthalate, shellac or the like, or given a sugar coating using a sugar coating liquid containing saccharose, sugar alcohol, gum arabic powder, talc or the like, thus producing film-coated tablets or sugar-coated tablets. One solvent in this coating technique may be purified water, but an organic solvent such as an alcohol, a ketone, an ether or a chlorinated hydrocarbon, or a mixture thereof can also be used. For example, ethanol, acetone, methylene chloride or the like can be used as an organic solvent. Moreover, as the coating apparatus, an apparatus ordinarily used in coating techniques for manufacturing medicines can be used, with examples including a spray coating apparatus in which the coating is carried out by spraying a coating liquid or the like, and a rotor fluidized bed granulator for layering.

In the case of manufacturing capsule preparations, capsule preparations can be manufactured by filling sustained release granules or immediate-release granules as above, or mini-tablets into hard gelatin capsules or HPMC capsules using an automatic capsule filling machine. Alternatively, in the case of the preparations for per-tube administration or a dry syrup that is used mixed with water or the like when taken, sustained-release granules or immediate-release granules as above can be mixed with a thickener or a dispersant so as to disperse these granules, the mixture then being made into granules or tablets. Furthermore, a liquid or jelly can be made using water, and substances selected from dispersants, emulsifiers, thickeners, preservatives, pH adjustors, sweeteners, flavorings, fragrances and so on. However, with respect to other manufacturing methods, there are no limitations to the above.

In order that embodiments described herein may be more fully understood, the following examples are set forth. It should be understood that these examples are for illustrative purposes only and are not to be construed as limiting.

EXAMPLES

Materials and Methods
Compounds and Drugs

Compound 1 is a selective, orally bioavailable small molecule FGFR4 inhibitor that is being developed by H3 Biomedicine. Lenvatinib is an FDA approved multi-receptor tyrosine inhibitor. Lenvatinib was administered as a mesylate salt, and Compound 1 was administered as a free base.
Cell Lines Tested The cell line used, Hep3B (also called HEP3B.1-7), was sourced from American Type Culture Collection (ATCC), verified free of mycobacterium contamination and verified for identity by short tandem repeat analysis of 9 markers.
Hep3B Xenograft Generation For the human hepatocellular cancer cell line Hep3B xenografts, Hep3B cells were cultured in RPMI1640 medium containing 10% FBS at 37° C. in a 5% $CO_2$ atmosphere and kept in exponential growth phase. For harvesting, the cells were washed with PBS, incubated with 0.25% trypsin-EDTA, and suspended in a 1:1 mixture of RPMI1640 medium containing 10% FBS. To prepare the inoculum at a final concentration of $5\times10^7$ cells/mL, the cell were spun and resuspended in RPMI1640 and Matrigel (Corning). To generate xenografts, 0.1-mL of the inoculum was injected subcutaneously into the right flank region of BALB/c nu/nu female mice, approximately 8-week-old, weighing 18-20 g, giving a final concentration of $5\times10^6$ cells/mouse.
LIX125 Patient Derived Xenograft (PDX) Generation The human primary hepatocellular model LIX125 from ChemPartner (shangpharma.com) was implanted into the female severe combined immunodeficiency (SCID) mice. When the tumors developed in mice, they were sacrificed and the resected tumors were implanted into female NU/NU mice for tumor preservation, histological diagnosis and in vivo efficacy study. Solid tumor tissues were depleted of necrotic components, cut into 10-15 mg pieces and mixed. Three to five pieces were mixed with 15-30 mL Matrigel and implanted into a flank of 6-8 week old female NU/NU immune compromised mice weighing 18-20 g. All of the primary tumors utilized in this study had undergone 3 to 5 passages in vivo and the tumor histology of each was maintained over the serial transplantation.
Dosing and Measurement of Antitumor Activity When the mean tumor volume (TV) reached approximately 170 $mm^3$ (10 days after implantation), mice were selected based on their TVs, and were sorted into multiple treatment groups with 8 animals per group. Per os (PO) treatment with Compound 1 (300 mg/kg for Hep3B and 500 mg/kg for LIX125) alone or in combination with lenvatinib vehicle (control) or lenvatinib (10 mg/kg or 3 mg/kg) administered once daily (QD). Additional groups included treatment with lenvatinib (10 mg/kg or 3 mg/kg) in combination with Compound 1 vehicle. (Lenvatinib vehicle includes the vehicle in which lenvatinib is administered; but, without any lenvatinib. Likewise, Compound 1 vehicle includes the vehicle in which Compound 1 is administered; but, without any Compound 1.)

The administration volume (0.1 mL/10 g body weight) was calculated from the individual mouse body weight (BW) before administration. Body weights were measured daily and tumor measurements were performed twice weekly. Mice with >20% body weight loss compared with their day 1 body weight or bearing tumors with the longest diameter >2,000 mm were immediately euthanized to prevent any pain or suffering for the animal.

Figure 1:
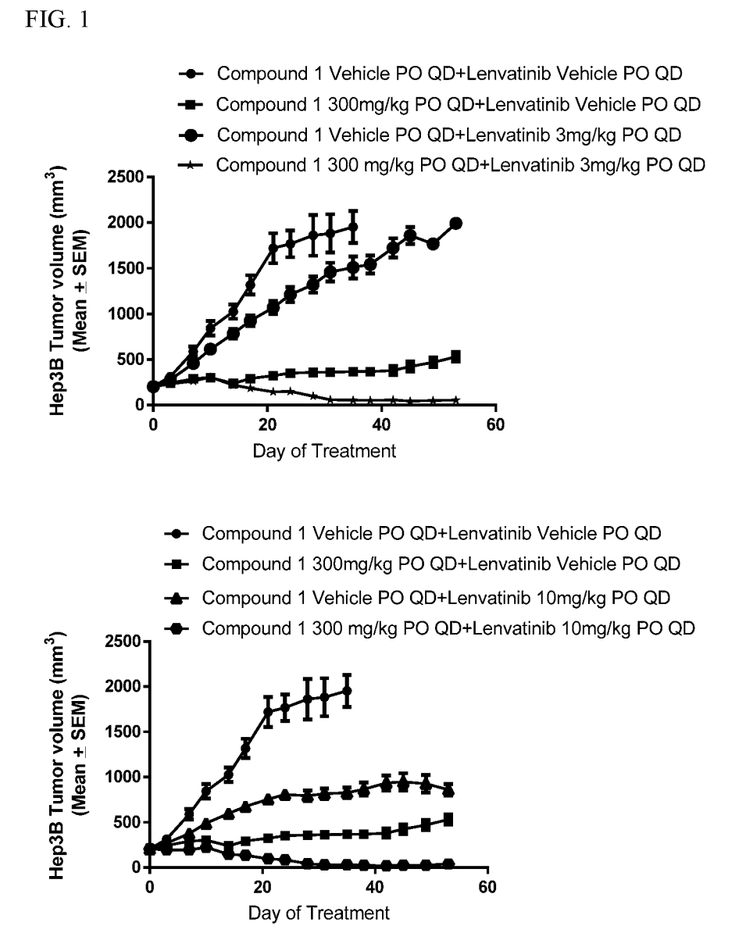
FIG. 1 shows antitumor effects of Compound 1 and lenvatinib in the Hep3B xenograft model of hepatocellular carcinoma. Both Compound 1 and lenvatinib were given orally (PO) once daily (QD) for 53 days. Data represent the mean±SEM for Tumor Volume.

The tumor volume (TV) in $mm^3$ was calculated according to the following formula: TV=length×width$^2$×0.5 length: largest diameter of tumor (mm) width: diameter perpendicular to length (mm). The tumor growth inhibition % (TGI) was calculated according to the following formula: Tumor growth inhibition % (TGI)=[(Average control TV day X−Treatment TV day X)/(Average control TV day X)]×100, where day X is any day of the treatment. The antitumor effects of the treatment, partial regression (PR) and complete regression (CR), stable disease (SD), and progressive disease (PD) were defined as follows:

PD: 3 consecutive measurements >120% of starting volume or 3 consecutive increasing measurements from best response; SD: 3 consecutive measurements >50% and <120% of starting volume; PR: 3 consecutive measurements <50% of starting volume; CR: 3 consecutive measurements <30 $mm^3$.
Statistical Analysis Data represent the mean±SEM for tumor volume (N=8). The differences in TV between groups were analyzed by multiple unpaired t-tests with significance determined using the Holm-Sidak method. Statistical analyses were performed using the GraphPad Prism version 7 (GraphPad Software, La Jolla, CA).
Results Example 1: Hep3B Cells Xenograft in Vivo Study To determine whether lenvatinib enhances tumor growth inhibition (TGI) exerted by Compound 1, the Hep3B cell line was grown as a xenograft in female nude immunocompromised mice. Tumor bearing mice were orally treated daily for 53 days with (a) 300 mg/kg Compound 1 as single agent with lenvatinib vehicle; (b)(i) 10 mg/kg lenvatinib as a single agent with Compound 1 vehicle; (b)(ii) 3 mg/kg lenvatinib as a single agent with Compound 1 vehicle; (c)(i) 300 mg/kg Compound 1 and 10 mg/kg lenvatinib in combination; or (c)(ii) 300 mg/kg Compound 1 and 3 mg/kg lenvatinib in combination. Results are shown in FIG. 1.

The single agent Compound 1 at 300 mg/kg resulted in inhibition of tumor growth with TGI of 81%, in comparison to the vehicle control (P<0.00001). Lenvatinib, as single agent at 10 mg/kg inhibited tumor growth with 58% TGI in comparison to the vehicle controls (P<0.00005). Lenvatinib, as single agent at 3 mg/kg inhibited tumor growth in this Hep3B model with 23% TGI in comparison to the vehicle controls (P>0.05). The combination of 300 mg/kg Compound 1 and 10 mg/kg lenvatinib resulted in enhancement of tumor growth inhibition in comparison to single agent groups with TGI of 98%. (P<0.00001). The combination of 300 mg/kg Compound 1 and 3 mg/kg lenvatinib also resulted in enhancement of tumor growth inhibition in comparison to single agent groups with TGI of 97%. (P<0.00001). These data demonstrate that lenvatinib can enhance the antitumor effects of Compound 1.

Treatment with Compound 1 as a single agent caused 2/8 SD and 6/8 PD in this model. Treatment with 10 mg/kg lenvatinib as a single agent caused 8/8 PD in this model. Treatment of 3 mg/kg lenvatinib as a single agent caused 8/8 PD in this model. Treatment with Compound 1 in combination with lenvatinib 10 mg/kg caused 4/8 CR and 4/8 SD in this model. Treatment with Compound 1 in combination with lenvatinib 3 mg/kg caused 3/8 CR and 5/8 SD in this model.

All combination dosing groups were well tolerated based on body weight measurements and routine clinical observation.

Example 2: PDX Xenograft in Vivo Study

Cell Line Maintenance

Figure 2:
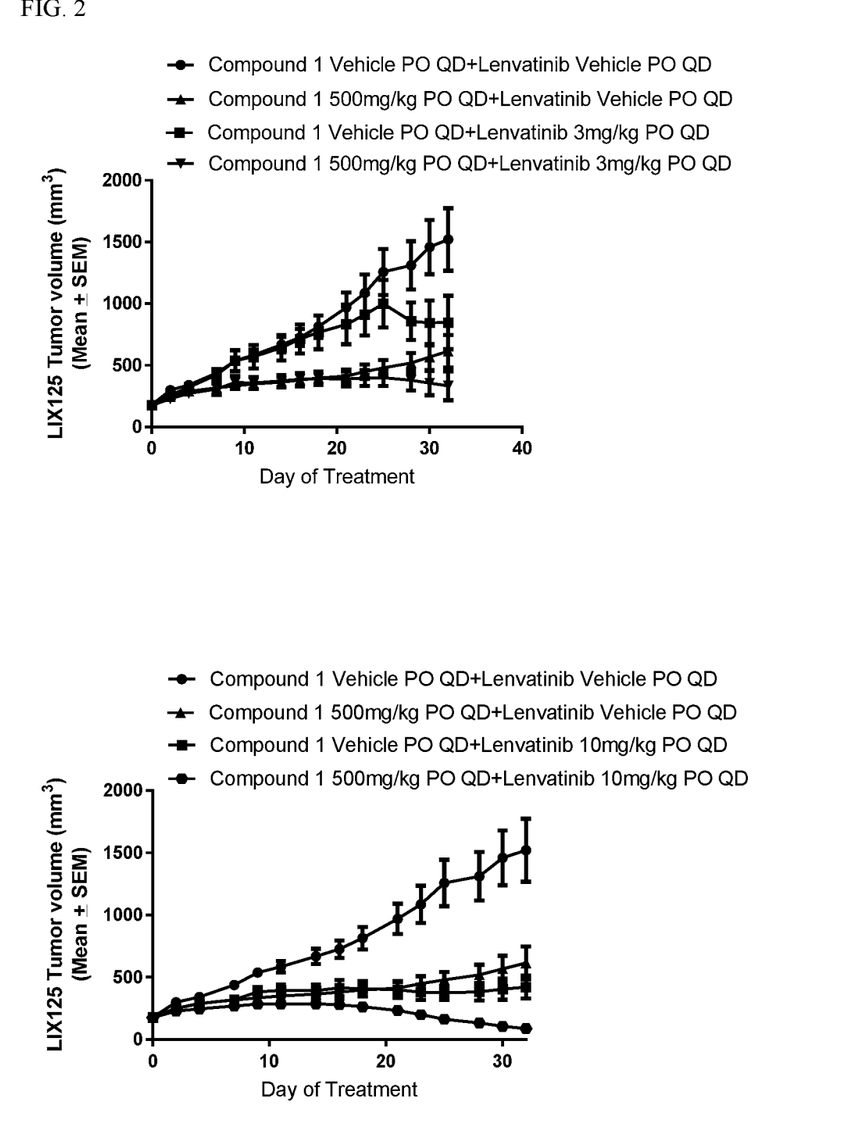
FIG. 2 shows results of a PDX xenograft in vivo study reported in Example 2.

To determine whether lenvatinib enhances tumor growth inhibition (TGI) exerted by Compound 1 in PDX models, NU/NU female mice were inoculated subcutaneously on the right flank with fragments of LIX125, a hepatocellular carcinoma patient derived xenograft (PDX) model. When the LIX125 tumor volumes were 100-300 mm3, the animals were randomized into six different groups with eight animals in each group. Tumor bearing mice were orally treated daily for 32 days with (a) 500 mg/kg Compound 1 as single agent with lenvatinib vehicle; (b)(i) 10 mg/kg lenvatinib as a single agent with Compound 1 vehicle; (b)(ii) 3 mg/kg lenvatinib as a single agent with Compound 1 vehicle; (c)(i) 500 mg/kg Compound 1 and 10 mg/kg lenvatinib in combination; or (c)(ii) 500 mg/kg Compound 1 and 3 mg/kg lenvatinib in combination; (d) Compound1 vehicle and Lenvatinib vehicle. Results are shown in FIG. 2.

Lenvatinib, as a single agent, significantly inhibited tumor growth at the 10 mg/kg dose but not at 3 mg/kg dose (p<0.0007 and p>0.05 respectively) in comparison to the vehicle control, with 72% and 44% TGI respectively. The single agent Compound 1 at 500 mg/kg did not significantly inhibit tumor growth (p>0.05) in comparison to the vehicle controls, with 60% TGI.

The combination of 500 mg/kg Compound 1 and 10 mg/kg lenvatinib resulted in significant enhancement of tumor growth inhibition (p<0.005) in comparison to 500 mg/kg of Compound 1 alone with TGI of 94%. This combination led to SD in 3/8 animals, PR in 4/8 animals, and PD in 1/8 animals. The combination of 500 mg/kg Compound 1 and 3 mg/kg lenvatinib did not result in significant enhancement of tumor growth inhibition (p>0.05) in comparison to 500 mg/kg of Compound 1 alone with TGI of 78%. This combination led to SD in 2/8 animals and PD in 6/8 animals. In general, the combination is well tolerated.

Consistent with the notion that lenvatinib can enhance Compound 1 effect in HCC models, additional testing in more HCC patient derived models showed enhancement in 4/6 models. All PDX models referenced herein are FGF19 expressing.

We claim:

1. A method of treating hepatocellular carcinoma in a patient in need thereof, comprising administering to the patient a combination of N-(2-((6-(3-(2,6-dichloro-3,5-dimethoxyphenyl)-1-methylureido)pyrimidin-4-yl)amino)-5-(4-ethylpiperazin- 1-yl)phenyl)acrylamide or a pharmaceutically acceptable salt thereof and 4-[3-chloro-4-(N'-cyclopropylureido)phenoxy]-7-methoxyquinoline-6-carboxamide or a pharmaceutically acceptable salt thereof, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof is administered in a daily dosage between 50 mg to 600 mg.

2. The method of claim 1, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof is administered in a daily dosage between 200 mg to 400 mg.

3. The method of claim 2, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof is administered in a daily dosage of 300 mg.

4. The method of claim 1, wherein the 4-[3-chloro-4-(N'-cyclopropylureido)phenoxy]-7-methoxyquinoline-6-carboxamide or pharmaceutically acceptable salt thereof is administered in a daily dosage of 8 mg.

5. The method of claim 1, wherein the 4-[3-chloro-4-(N'-cyclopropylureido)phenoxy]-7-methoxyquinoline-6-carboxamide or pharmaceutically acceptable salt thereof is administered in a daily dosage of 12 mg.

6. The method of claim 1, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and the 4-[3-chloro-4-(N'-cyclopropylureido)phenoxy]-7-methoxyquinoline-6-carboxamide or a pharmaceutically acceptable salt thereof are administered as separate formulations.

7. The method of claim 1, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and the 4-[3-chloro-4-(N'-cyclopropylureido)phenoxy]-7-methoxyquinoline-6-carboxamide or a pharmaceutically acceptable salt thereof are administered as a single formulation.

8. The method of claim 1, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and the 4-[3-chloro-4-(N'-cyclopropylureido)phenoxy]-7-methoxyquinoline-6-carboxamide or a pharmaceutically acceptable salt thereof are administered sequentially.

9. The method of claim 1, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and the 4-[3-chloro-4-(N'-cyclopropylureido)phenoxy]-7-methoxyquinoline-6-carboxamide or a pharmaceutically acceptable salt thereof are administered simultaneously.

10. The method of claim 1, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide is in free base form.

11. The method of claim 1, wherein the pharmaceutically acceptable salt of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide is a free base form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide.

12. The method of claim 1, wherein the pharmaceutically acceptable salt of 4-[3-chloro-4-(N'-cyclopropylureido)phenoxy]-7-methoxyquinoline-6-carboxamide is a mesylate salt of 4-[3-chloro-4-(N'-cyclopropylureido)phenoxy]-7-methoxyquinoline-6-carboxamide.

13. The method of claim 1, wherein the pharmaceutically acceptable salt of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide is a free base form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide, and wherein the pharmaceutically acceptable salt of 4-[3-chloro-4-(N'-cyclopropylureido)phenoxy]-7-methoxyquinoline-6-carboxamide is a mesylate salt of 4-[3-chloro-4-(N'-cyclopropylureido)phenoxy]-7-methoxyquinoline-6-carboxamide.

14. A pharmaceutical formulation comprising N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof, 4-[3-chloro-4-(N'-cyclopropylureido)phenoxy]-7-methoxyquinoline-6-carboxamide or a pharmaceutically acceptable salt thereof, and a pharmaceutically acceptable carrier.

15. The pharmaceutical formulation of claim 14, comprising a free base form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide.

16. The pharmaceutical formulation of claim 14, wherein the pharmaceutically acceptable salt of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide is a free base form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide.

17. The pharmaceutical formulation of claim 14, wherein the pharmaceutically acceptable salt of 4-[3-chloro-4-(N'-cyclopropylureido)phenoxy]-7-methoxyquinoline-6-carboxamide is a mesylate salt of 4-[3-chloro-4-(N'-cyclopropylureido)phenoxy]-7-methoxyquinoline-6-carboxamide.

18. The pharmaceutical formulation of claim 14, wherein the pharmaceutically acceptable salt of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide is a free base form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide, and wherein the pharmaceutically acceptable salt of 4-[3-chloro-4-(N'-cyclopropylureido)phenoxy]-7-methoxyquinoline-6-carboxamide is a mesylate salt of 4-[3-chloro-4-(N'-cyclopropylureido)phenoxy]-7-methoxyquinoline-6-carboxamide.

* * * * *